United States Patent
Hoftman et al.

(10) Patent No.: US 9,522,043 B1
(45) Date of Patent: Dec. 20, 2016

(54) STORAGE AND PROTECTION DEVICE FOR BRONCHOSCOPES

(71) Applicant: Advanced Medical Innovations, Inc., Northridge, CA (US)

(72) Inventors: Nir Hoftman, Los Angeles, CA (US); Carsten Nadjat-Halem, Los Angeles, CA (US); Aman Mahajan, Sherman Oaks, CA (US); Mike Hoftman, Calabasas, CA (US)

(73) Assignee: ADVANCED MEDICAL INNOVATIONS, INC., Northridge, CA (US)

( * ) Notice: Subject to any disclaimer, the term of this patent is extended or adjusted under 35 U.S.C. 154(b) by 60 days.

(21) Appl. No.: 13/914,411

(22) Filed: Jun. 10, 2013

Related U.S. Application Data

(60) Provisional application No. 61/689,721, filed on Jun. 11, 2012.

(51) Int. Cl.
*A61B 1/00* (2006.01)
*A61B 19/02* (2006.01)

(52) U.S. Cl.
CPC ................................. *A61B 19/0256* (2013.01)

(58) Field of Classification Search
CPC ... A61B 1/0014; A61B 19/26; A61B 18/1482; A61B 18/1492; A61B 1/2676; A61B 19/0256; F16M 13/022
USPC ............. 600/424, 102, 104; 248/295.11, 689
See application file for complete search history.

(56) References Cited

U.S. PATENT DOCUMENTS

| | | | | |
|---|---|---|---|---|
| 4,907,395 A * | 3/1990 | Opie | ................ | A61B 1/00142 206/364 |
| 6,656,199 B1 * | 12/2003 | Lafontaine | ........ | A61M 25/0127 606/191 |
| 8,317,149 B2 * | 11/2012 | Greenburg | ......... | A61B 1/00128 248/228.7 |
| 8,480,629 B2 * | 7/2013 | Crowley | ................ | A61B 50/20 604/174 |
| 2006/0235268 A1 * | 10/2006 | Elsie | .................. | A61B 1/00147 600/102 |
| 2010/0224187 A1 * | 9/2010 | Dalton | ............... | A61M 16/0488 128/200.26 |
| 2010/0228085 A1 * | 9/2010 | Mirza | .................... | A61B 1/018 600/106 |
| 2012/0323125 A1 * | 12/2012 | Driedger | ............. | A61B 1/0014 600/462 |
| 2015/0073211 A1 * | 3/2015 | Dickhans | ............. | A61B 1/0014 600/104 |

* cited by examiner

Primary Examiner — Todd M Epps

(57) ABSTRACT

The present invention is a storage and protection device for bronchoscopes having a protection tube of sufficient length to enclose at least a majority of a length of an insertion tube of a flexible bronchoscope. Extending upward from a top end of the protection tube is an upper structure support clamp adapted to releasably secure an upper structure of the flexible bronchoscope so that at least a majority of the length of the insertion tube lies within the protection tube. The upper structure support clamp connection with the upper structure of the bronchoscope preferably allows the insertion tube to hang freely within the protection tube when the protection tube is oriented substantially vertically.

18 Claims, 15 Drawing Sheets

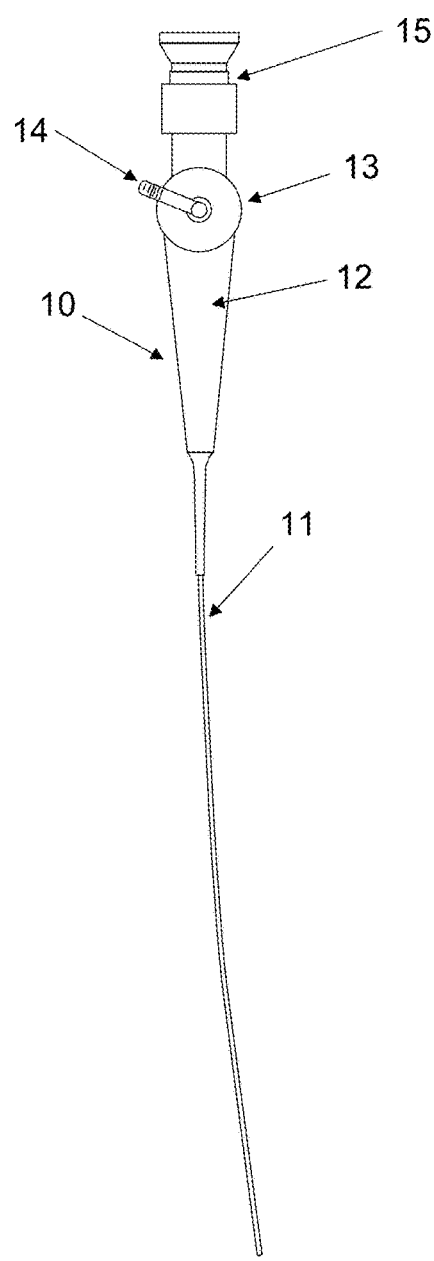
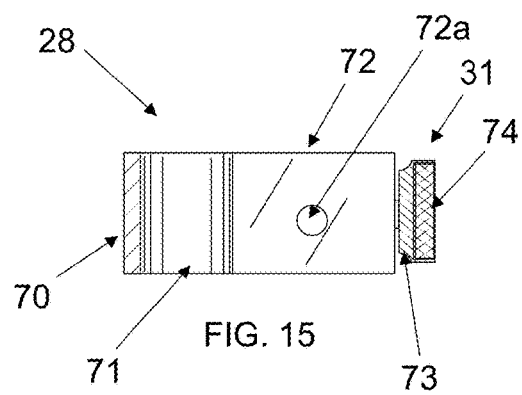
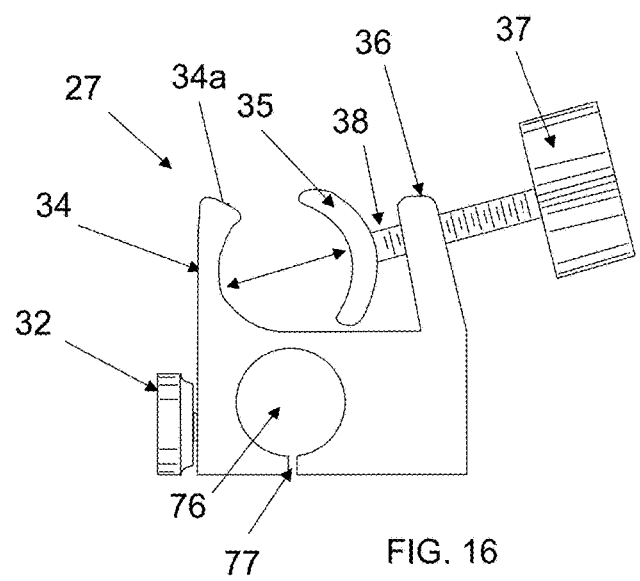
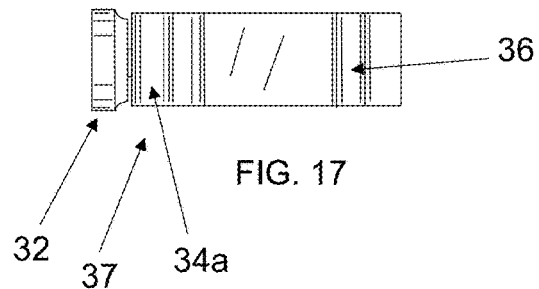
FIG. 14 - PRIOR ART
FIG. 15
FIG. 16
FIG. 17

STORAGE AND PROTECTION DEVICE FOR BRONCHOSCOPES

This application claims the benefit of a provisional application with Ser. No. 61/689,721 filed Jun. 11, 2012, which application is hereby incorporated herein by reference and from which priority is hereby claimed under 35 U.S.C. Sections 119(e) and 120.

FIELD OF THE INVENTION

The present invention relates to devices to store, transport and protect flexible fiberoptic or CCD (video chip) tipped bronchoscopes and other endoscopes.

BACKGROUND OF THE INVENTION

Bronchoscopy is a test to view the airways and diagnose lung disease. Currently, a device called a flexible bronchoscope is most often used to see the inside of the airways and lungs. The flexible bronchoscope comprises a thin insertion tube from 2.2 to 6 mm or larger in diameter and about 2 feet long. The insertion tube is desirably minimized in diameter to reduce patient distress. The insertion tube is typically inserted at a free end into a patient mouth, into an airway, and then into the lung. The delicate, vascularized tissues of these airways requires an insertion tube which is minimally rigid, maximally flexible and relatively delicate as to its optical elements to accomplish insertion and desired placement of the free end without injury. Thus, it is well known that the flexible bronchoscope is especially prone to damage to its insertion tube section when not in patient use.

FIG. 14 shows a prior art flexible bronchoscope 10 illustrating its major parts. The flexible bronchoscope 10 generally comprises an insertion tube 11 (with a free, insertion end), a flared transition 12 to a junction housing 13 (which usually includes an articulation lever 14), and an eyepiece 15. It is well known to extend from the junction housing additional connections for wires or fiberoptic strands so that light and/or signals (light or electrical) may be transmitted thereon to a camera, a video recorder, or a display screen that displays a view from the insertion end of the bronchoscope 10. FIG. 14 shows the typical orientation of the bronchoscope 10 during storage and transportation from storage to use. A user will often grasp the structures above the insertion tube 11 and allow the insertion tube to dangle freely, making it an easy target for impact with other more durable structures, devices or personnel. Even slight impact can have a devastating effect on the sensitive optical and electrical features of the flexible insertion tube 11. In the case of a fiberoptic bronchoscope, terminal ends of fiberoptic strands may be broken or abraded or scored or such strands might be broken within the insertion tube. In the case of a CCD-tipped flexible bronchoscope, the highly sensitive CCD chip located at the terminal end of the insertion tube may receive an impact which entirely or partly destroys its operation or fine electrical connections to more substantial wires.

Flexible bronchoscopes are very delicate instruments that require special care at all stages of handling to prevent equipment damage. Even the control levers (such as the articulation lever 14 of FIG. 14) can easily be damaged during storage, transportation, cleaning and use. It is well known that bronchoscopy carts adapted to be mobile, wheeled carts contain typically used bronchoscopy supplies and equipment and comprise rigid tubes permanently fixed to the cart sides. These rigid tubes receive the insertion tubes of flexible bronchoscopes and support the upper structure of the bronchoscopes by way of contact of an upper rim of the rigid tube with a portion of the flared transition 12. Thus, the prior art teaches that adequate protection for flexible bronchoscopes is achieved by way of locating the insertion tubes in the rigid tubes of the bronchoscope cart. The prior art has clearly failed to appreciate that this solution has not been adequate. The clinical storage, transportation, cleaning and storage of flexible bronchoscopes is far broader in scope than a brief transportation of the device in a bronchoscopy cart.

First, storage of flexible bronchoscopes between uses is accomplished in a metal cabinet with elevated pairs of hooks adapted to engage the flared transition 12 to allow the insertion tube to dangle freely within the cabinet, open to becoming tangled with other insertion tubes, impact from personnel activity within the cabinet, or impact when the bronchoscope is put into or taken out of the cabinet. The present inventors have discovered that flexible bronchoscopes are often damaged in the cabinets or while being transferred from the cabinet to the cart or vice versa.

Second, after use in a bronchoscope procedure, best practices dictate that bronchoscopes are not returned to the rigid tube of the bronchoscopy cart, but instead are place in a disposable tray so that patient fluids adhering to the insertion tube are not transmitted to the inside surface of the rigid tube, which is difficult to disinfect and/or visualize for contamination. Placing the bronchoscope in such an exposed location exposes it to unintended impacts and abrasion from instruments, trays, and movement of items onto and away from the cart.

After exposure to harm on or around the bronchoscopy cart, the bronchoscope is transported to a decontamination suite in the open tray. This transportation allows further impacts and/or abrasion. Even slight, unappreciated impacts to the insertion tube or other elements of the bronchoscope can result in very substantial damage, as currently determined by the inventors.

In the past, bronchoscopy carts have incorporated cameras and display screens allowing for seeing the images available at the terminal end of the insertion tube, which coincided with the availability of rigid tubes in which to locally and temporarily store bronchoscopes. However, audio/visual integration and miniaturization of cameras and video processing and viewing equipment will result in a decline of bronchoscopy carts, as such image recording and display equipment is now typically a part of bronchoscopy procedure rooms. Without the need to transport the heavy or bulky image recording and display equipment, transport of bronchoscopes will eventually be made by way of withdrawal from the storage cabinet and carrying the bronchoscope, with an unprotected insertion tube, to the procedure room.

In modern state of the art hospitals facilities most operating rooms have built in video processors and displays, such that bronchoscopy carts are mostly obsolete. Thus, when requesting a bronchoscope, only the device is brought into the room (no cart with video equipment needed). Given that the rigid tube protector is built into the cart, the scope now arrives unprotected and typically placed in a plastic tray. This activity results in increased risk to the bronchoscopes over the methods in the recent past for transportation. One single university hospital O.R. department responsible for bronchoscopy on average spends $120,000 on annual bronchoscope repairs, the vast majority required due to equipment damage. Other endoscopic devices, such as transesophageal echo (TEE) probes, undergo a similar clinical usage regimen. Thus, there is a need for a storage and transportation device for bronchoscopes which reduces or eliminates potential harm to its impact sensitive components, while complying with industry infection control and safety standards.

SUMMARY OF THE INVENTION

The present invention is a storage and protection device for bronchoscopes having a protection tube of sufficient length to enclose at least a majority of a length of an insertion tube of a flexible bronchoscope. Extending upward from a top end of the protection tube is an upper structure support clamp adapted to releasably secure an upper structure of the flexible bronchoscope so that at least a majority of the length of the insertion tube lies within the protection tube. The upper structure support clamp connection with the upper structure of the bronchoscope preferably allows the insertion tube to hang freely within the protection tube when the protection tube is oriented substantially vertically. That same connection essentially prevents shifting of the upper structure of the bronchoscope during transportation or storage of the combination bronchoscope, essentially eliminating any damaging impact of the insertion tube during those activities.

A preferred form of the invention for the upper structure support clamp comprises a height adjuster part that releasably connects with an upper part of the protection tube. From the height adjuster part extends upward a vertical support bar, to whose end is fixed a scope clamp, which preferably comprises a pair of padded, spring compressed jaws for engaging the upper structure of the bronchoscope and a pair of handles which can be compressed by a user's hand to release said spring compression. The height adjuster part is adapted by way of screws, bolts or the like to be released from supportive connection with the protection tube to be moved up or down relative to the protection tube, thereby resulting in a higher of lower position of the scope clamp, which in turn results in a higher or lower position of the upper structure of the bronchoscope when engaged with the scope clamp.

Transportation of the bronchoscope engaged in the invention device requires no special training. A user can grasp the protection tube and/or upper structure support clamp and safely carry or place in storage the entire assembly. That entire assembly, due to the effective connection of the scope clamp to the upper structure of the bronchoscope, can be carried vertically with the support structure at a highest position, horizontal, or vertically with the support structure in a lowest position (upside down) with the same level of protection for the insertion tube. The upper structure support clamp provides a skeletal superstructure about the sensitive parts of the upper structure of the bronchoscope and prevents damaging impacts thereto.

Engagement of the bronchoscope with the invention storage and protection device is similarly simple and easy to accomplish. A user holding the invention device vertically at the scope clamp guides the insertion tube into the top opening of the protection tube. When the upper structure of the bronchoscope reaches the scope clamp, the user opens the padded jaws of the scope clamp and releasably engages the upper structure of the bronchoscope. The bronchoscope is then protected and engaged with the invention device. Releasing the bronchoscope from the invention device proceeds in reverse order, with the user grasping the scope clamp to release the upper structure of the bronchoscope from the scope clamp and thereafter carefully withdrawing the insertion tube from the protection tube.

In a further embodiment of the invention, the protection tube is provided with a pole support clamp, which is optionally releaseable or moveable up or down the length of the protection tube. The pole support clamp is adapted to releasably clamp to an IV pole or similar pole (such as a bed frame or other vertical pole or bar) so that the protection tube is maintained in a vertical position. An alternate form of this embodiment is to provide the protection tube with two or more spaced apart magnetic supports that together magnetically attach to a vertical metal surface (such as a bronchoscopy cart, a bed frame, or structures often available in a procedure room) whereby the attachment of the two magnetic supports to the vertical metal surface results in vertical alignment of the protection tube. Such vertical attachment means for the protection tube may also be accomplished by way of hooks, latches, or hook and loop connector strips.

Another embodiment of the invention device recognizes that additional structures extend from the junction housing of the bronchoscope in the form of cables, wires, small tubes, and similar flexible structures. These additional structures typically terminate at 1-3 feet from the junction housing, forming a substantial mass and volume to be transported and stored with the invention device. In this embodiment, a carrier bag (preferably of a disposable clear plastic with a drawstring) gathers the rolled or folded additional structures into the carrier bag, whereafter the carrier bag is suspended from a hook or other releaseable engagement structure on the protection tube. Thus, in this embodiment, the mass and volume of the additional structures extending from the junction housing of the bronchoscope are stabilized and easily carried with the bronchoscope engaged with the invention device. In a preferred form of this embodiment, the carrier bag is disposed of during a cleaning and decontamination process and a new carrier bag is used for later transport and storage of the bronchoscope and the engaged invention device.

The invention device comprises additional embodiments to reduce contamination by body fluids after a bronchoscopy procedure. An internal flexible liner covering the internal surfaces of the protection tube and disposable covers for jaws of the scope clamp are provided after patient use of the bronchoscope so that they may be disposed and replaced at a cleaning or decontamination step. In the embodiments relating to flexible liners for the interior surface of the protection tube, flexible liners may either be open from a top of the protection tube to the bottom of the protection tube or may have a seal at a location just above a bottom end of the protection tube when the flexible liner is appropriately applied to the protection tube. The un-sealed flexible liner allows for a cleaned and decontaminated insertion tube, while still in a partly wetted state, to air dry as it would in prior art storage in a storage cabinet. The sealed flexible liner is used at some time just before the insertion tube is protected by the invention device just before, during, and after a patient procedure to prevent dripping of body fluids from the bottom of the protection tube. Alternately, an unsealed liner whose bottom end extends beyond a bottom end of the protection tube may be effectively sealed by clamping or lifting the bottom end of the flexible liner up and taping or attaching it securely to an outside surface of the bottom section of the protection tube.

An object of the invention is to provide a mobile storage and protection device for bronchoscopes, where a protection tube is provided with means for supporting the upper structure of a bronchoscope above a top opening of the protection tube.

A further object of the invention is to provide a mobile storage and protection device for bronchoscopes, where disposable covers are provided for an internal surface of a protection tube and or contact surfaces of a scope clamp supported above a top opening of the protection tube.

BRIEF DESCRIPTION OF THE DRAWINGS

FIG. 14 is a side view of a generalized prior art bronchoscope.

FIG. 15 is a cutaway side view of a magnetic support of the device of FIG. 1.

FIG. 16 is a top view of a combined pole clamp and magnetic support of the device of FIG. 1.

FIG. 17 is a side view of the combined clamp of FIG. 15 without a portion of the pole clamp.

DETAILED DESCRIPTION OF THE INVENTION

Figure 1:
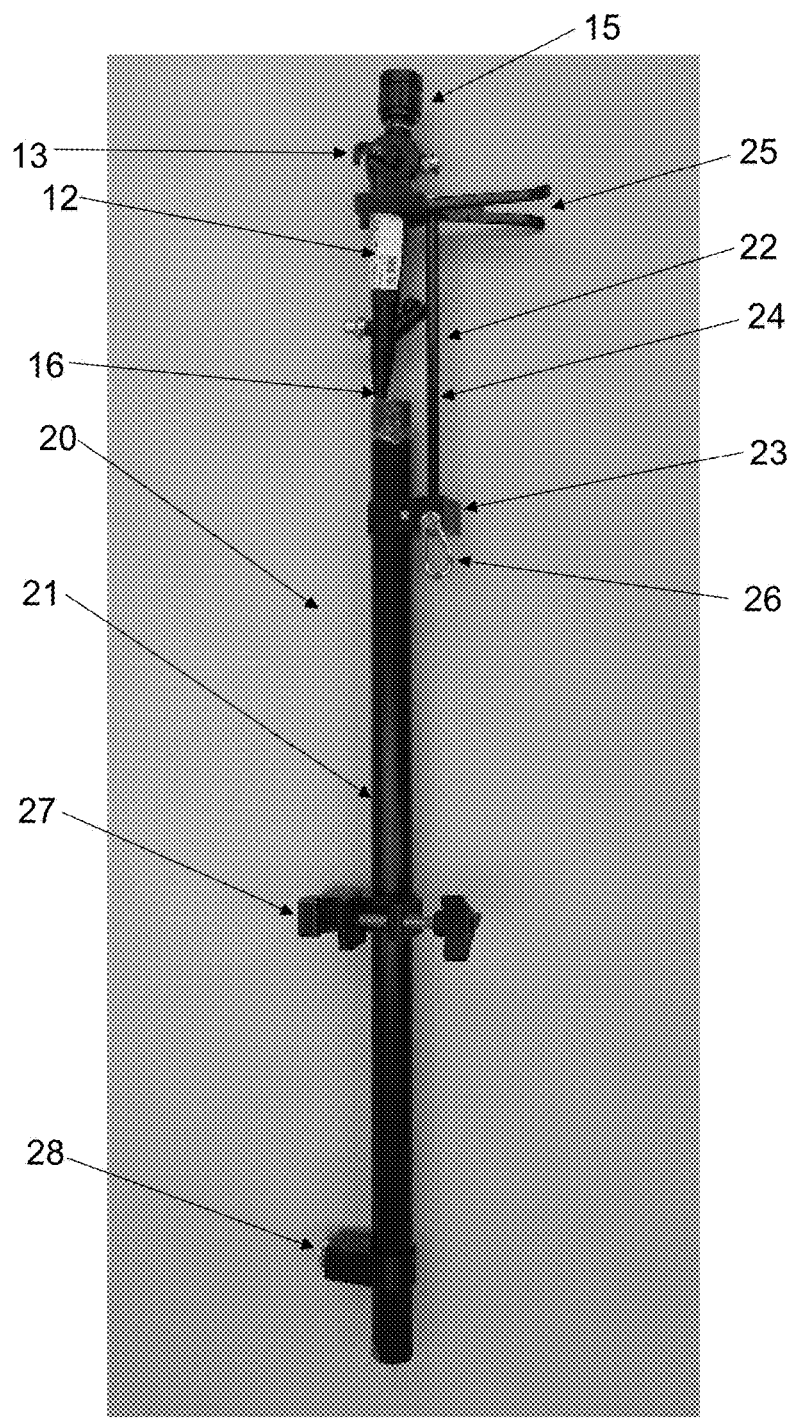
FIG. 1 is a side view of a bronchoscope engaged with the invention storage and protection device with the upper structure of the bronchoscope supported at an elevation above a top opening of a protection tube by an upper support clamp.

FIG. 1 is a side view of a bronchoscope 10 engaged with the invention storage and protection device 20 with the upper structure of the bronchoscope supported at an elevation above a top opening of a protection tube 21 by an upper support clamp 22. The upper support clamp 22 in this embodiment comprises a scope clamp 25, a support bar 24, and an adjustable protection tube clamp 23, which releasably fixes the upper support clamp 22 to the upper end of the protection tube 21. The protection tube 21 further provides a combination magnetic connector and IV pole clamp 27 and a magnetic connector 28. An upper structure of the bronchoscope 10 comprises an eyepiece (through which a user can view what is visible at a terminal end of an insertion tube), a junction housing 13, and a flared transition 12, where the scope clamp 25 is shown securely but releasably holding the upper structure of bronchoscope 10 so that the flared transition 12 is held oriented essentially axially with an axis of the protection tube 21, whereby an insertion tube extends into the protection tube 21 from an end 16 of the flared transition 12.

Figure 2:
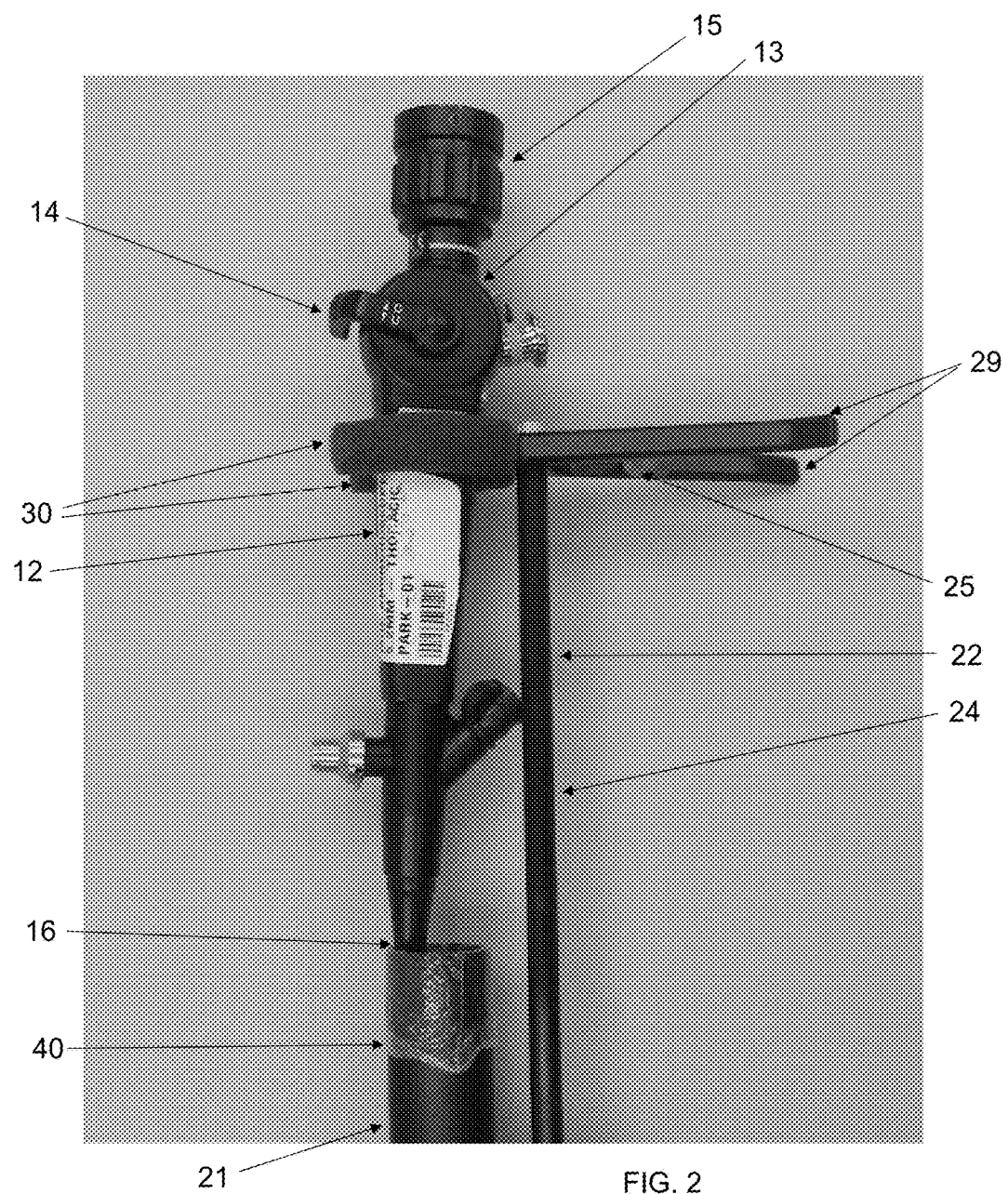
FIG. 2 is a close up view of an upper part of the invention device of FIG. 1.

FIG. 2 is a close up view of an upper part of the invention device 20 of FIG. 1, where scope clamp 25 is shown further comprising handles 29 urged apart by a spring between them and which pivot at a pivot point to urge padded jaws 30 together about the upper structure of the bronchoscope 10, more specifically about an upper part of the flared transition 12. A part of a flexible liner 40 is shown folded back upon an outside surface of protection tube 21 after internally lining an inside surface of protection tube 21.

Figure 3:
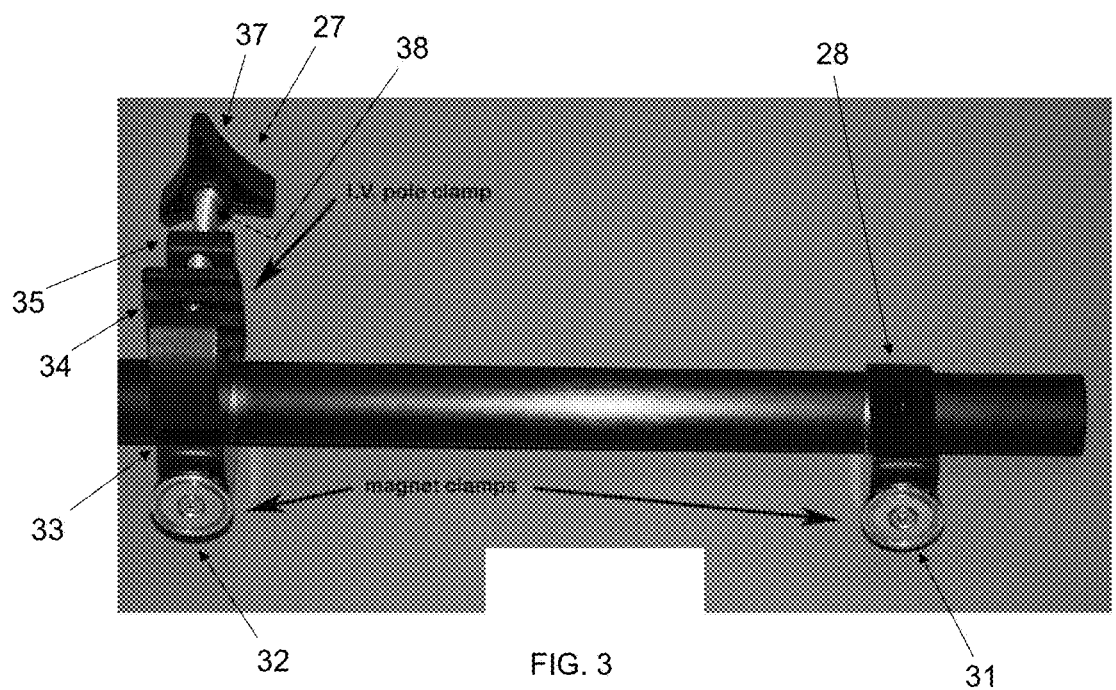
FIG. 3 is a close up view of a lower part of the invention device of FIG. 1 showing a pole clamp and two magnetic supports.

FIG. 3 is a close up view of a lower part of the invention device of FIG. 1 showing a pole clamp 27 and a magnetic support 28, where pole clamp 27 has an integral magnetic support magnet 32 integral with it. Magnetic support 28 also comprises a magnet 31, whereby the two magnets 31 and 32 attached to a vertical metal surface are sufficiently strongly connected to that surface to support the entire weight of the invention device 20 and bronchoscope 10 engaged with it in a vertical position as in FIG. 1 and FIG. 6A (to surface 50 at the metal side of an anesthesia machine), 6B (to surface 51 adjacent to a metal frame portion of a video support boom), and 6C (to surface 52 at the metal side of an O.R. or bronchoscopy cart). Referring again to FIG. 3, pole clamp 27 further comprises opposing jaws 34 and 35 in which an IV pole can be secured by causing threaded shaft 38 to rotate within a threaded bore in extension 36 by turning handle 37.

Figure 4:
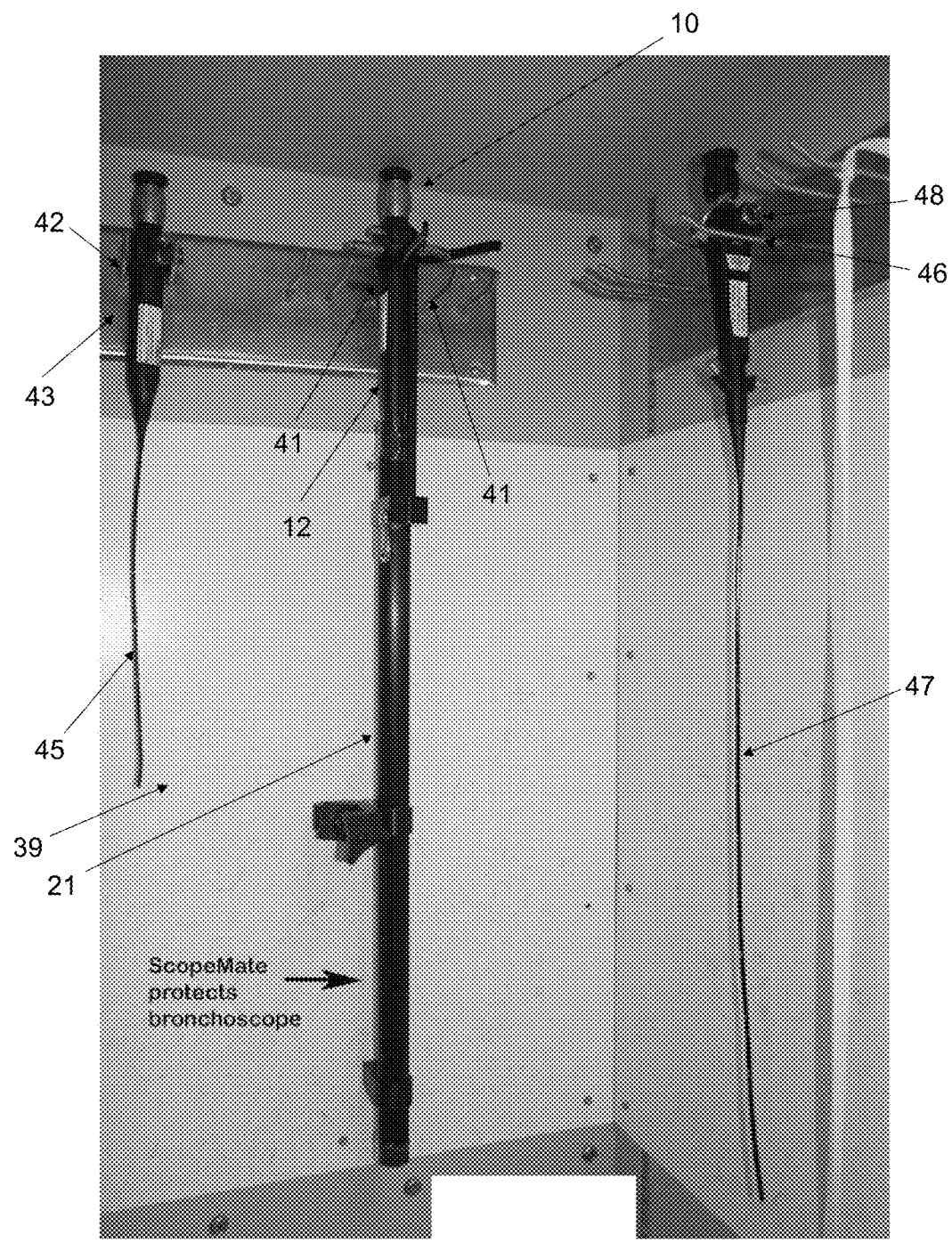
FIG. 4 shows the device of FIG. 1 in a storage cabinet with unprotected bronchoscopes.

FIG. 4 shows the device 20 and bronchoscope 10 of FIG. 1 in a storage cabinet with unprotected bronchoscopes 43 and 48 hanging respectively from hooks 42 and 46 and having their insertion tubes 45 and 47 exposed to impact damage by placement in and removal from storage cabinet 39. Invention device 20 comprises an upper support clamp structure that can supportively engage hooks 41 in the storage cabinet 39 to provide protection for the upper structure of the bronchoscope 10. Alternatively, invention device 20 comprises magnets that can attach to a ferrous metal structure that lines the inside wall of the storage cabinet to suspend the bronchoscope without the need for hooks.

Figure 5:
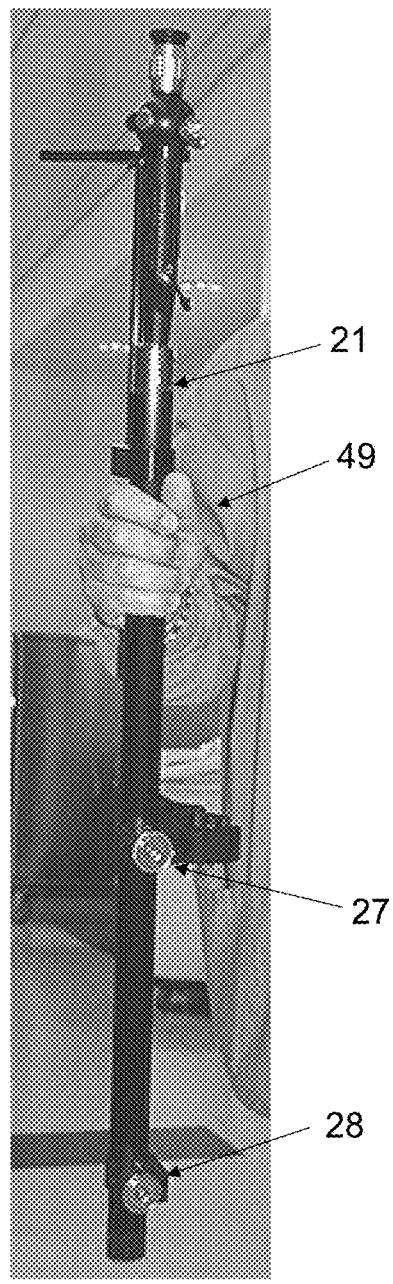
FIG. 5 shows the device of FIG. 1 grasped at the protection tube by a user.
Figure 7:
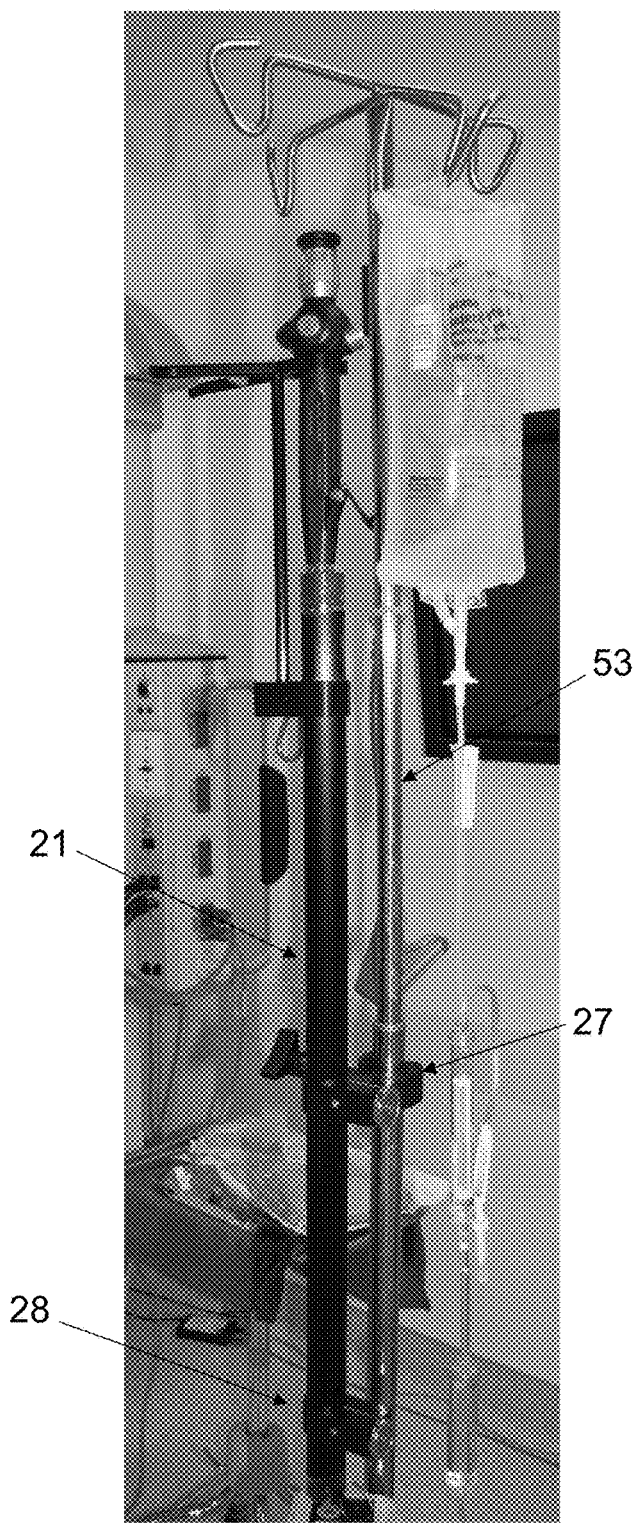
FIG. 7 shows the device of FIG. 1 releaseable and vertically fixed to an IV pole by a pole clamp.
Figure 8:
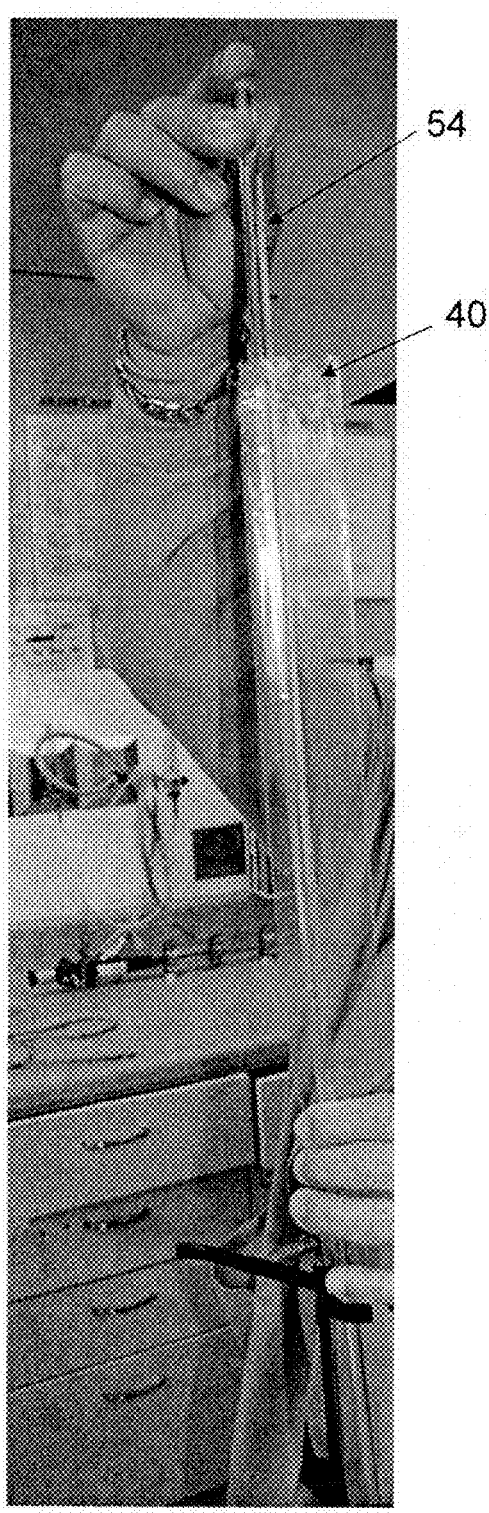
FIG. 8 is a side view of a user inserting a support rod into a flexible, disposable internal liner, whereafter the use shall insert the internal liner into a protection tube of the invention device of FIG. 1.
Figure 9A:
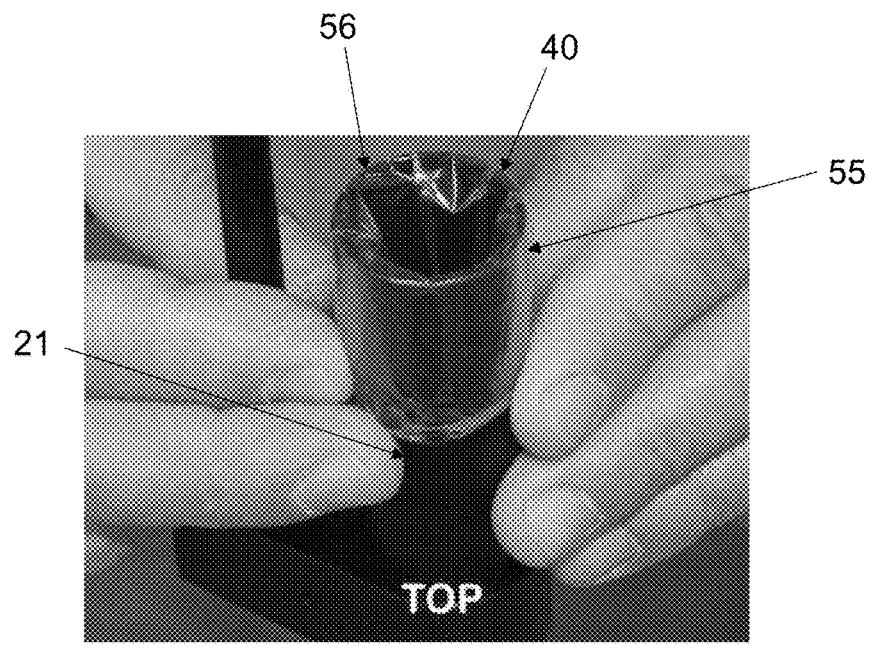
FIG. 9A shows a user after the internal liner of FIG. 8 has been inserted into a protection tube of FIG. 1 causing an upper end of the plastic liner to be folded over an outside surface of a top end of the protection tube.
Figure 9B:
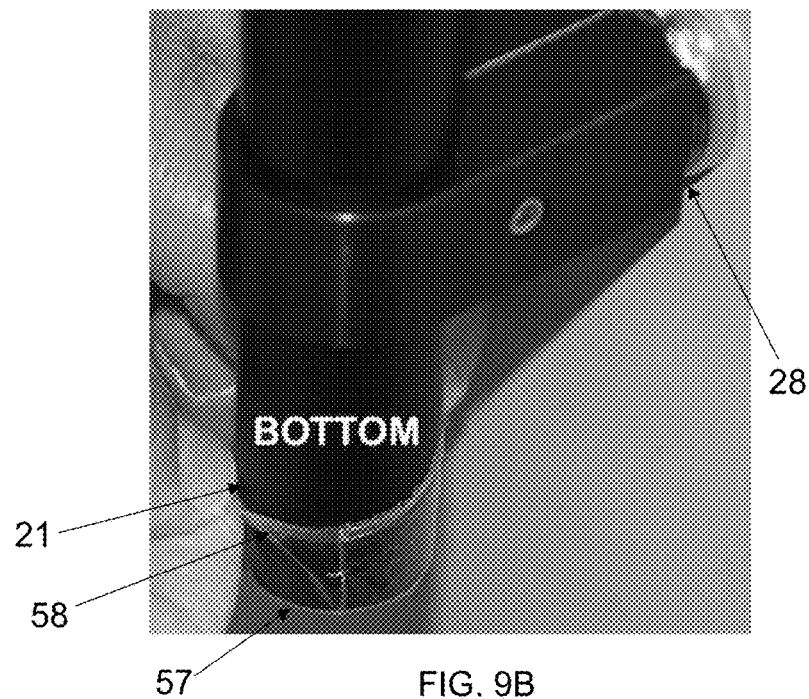
FIG. 9B shows a user after the internal liner of FIG. 8 has been inserted into a protection tube of FIG. 1 causing a lower end of the plastic liner to be folded over an outside surface of a bottom end of the protection tube.

FIG. 5 shows the invention device 10 of FIG. 1 grasped at the protection tube 21 by a user's hand 49. FIG. 7 shows the invention device 20 of FIG. 1 releasably and vertically fixed to an IV pole 53 by a pole clamp 27. FIG. 8 is a side view of a user inserting a support rod 54 into a flexible, disposable internal liner 40, whereafter the user shall insert the internal liner into a protection tube of the invention device of FIG. 1, using the rod supported liner 40 to overcome any resistance or friction opposing insertion of liner 40 into the protection tube. After the liner 40 is inserted into the protection tube 21, FIG. 9A shows that a portion 55 extends above a top end 56 of protection tube 21 which is preferably folded back over a top outside surface of protection tube 21 to reduce possibility of biological contamination from patient fluids on an insertion tube after a bronchoscopy procedure. Similarly, After the liner 40 is inserted into the protection tube 21, FIG. 9B shows that a portion 58 extends above a bottom end 57 of protection tube 21 which is preferably folded back over a top outside surface of protection tube 21 to reduce possibility of biological contamination from patient fluids on an insertion tube after a bronchoscopy procedure.

Figure 10:
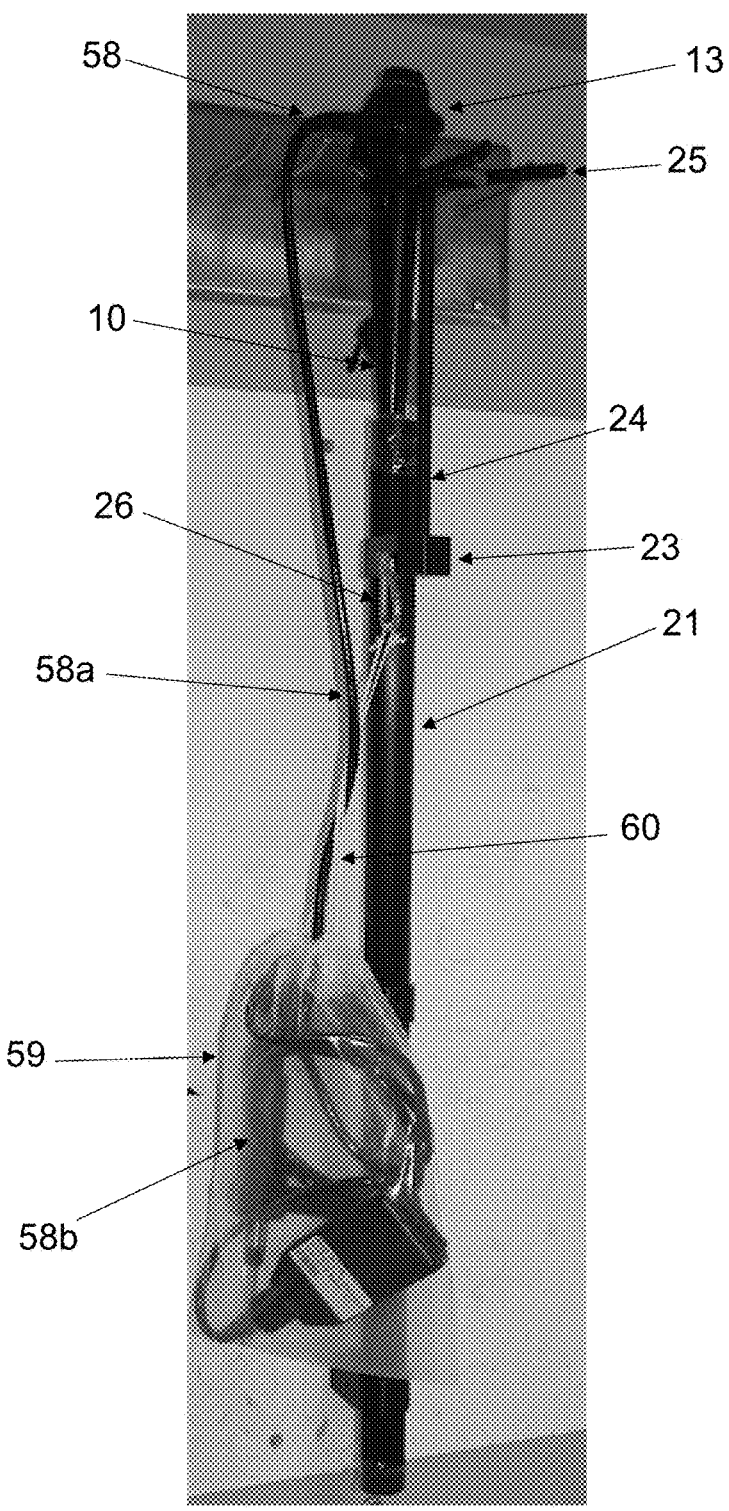
FIG. 10 shows the device of FIG. 1 where additional structure extends from a junction housing, is gathered into a carrier bag, and the carrier bag is suspended from a hook extending from a side of the protection tube.
Figure 11:
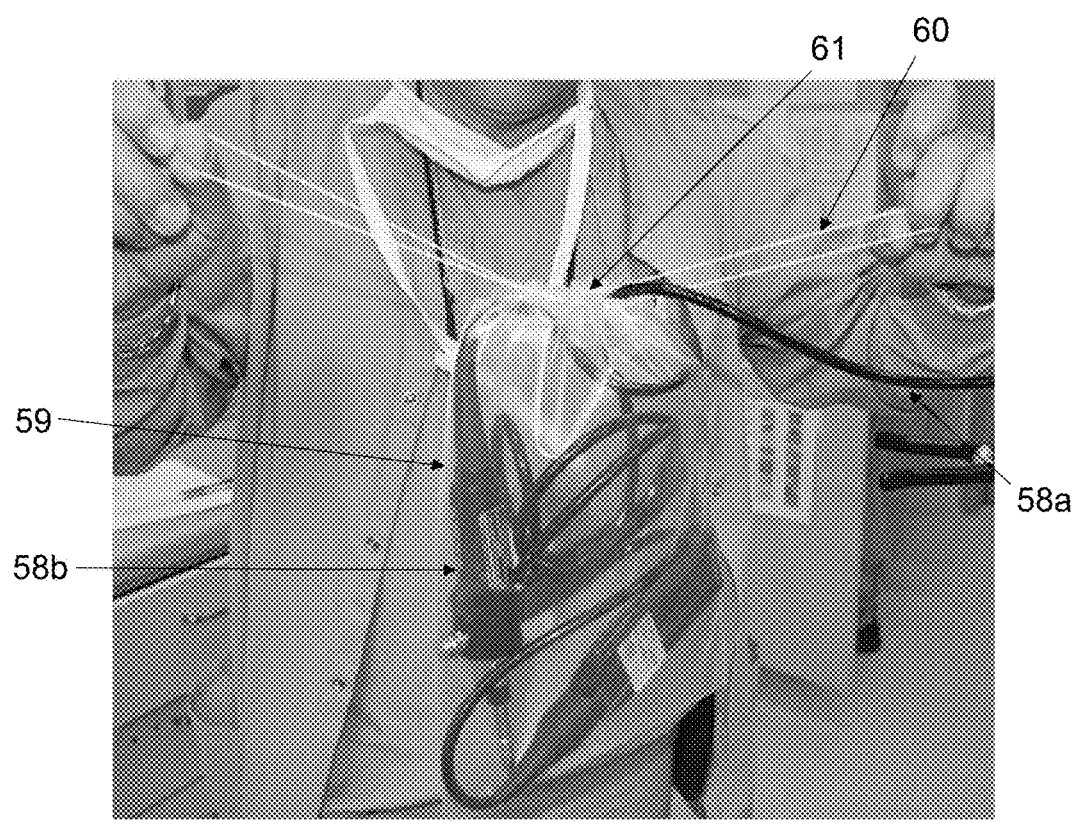
FIG. 11 shows a user having gathered the additional structure of FIG. 10 into the carrier bag drawing closed a drawstring at a top of the carrier bag.
Figure 12:
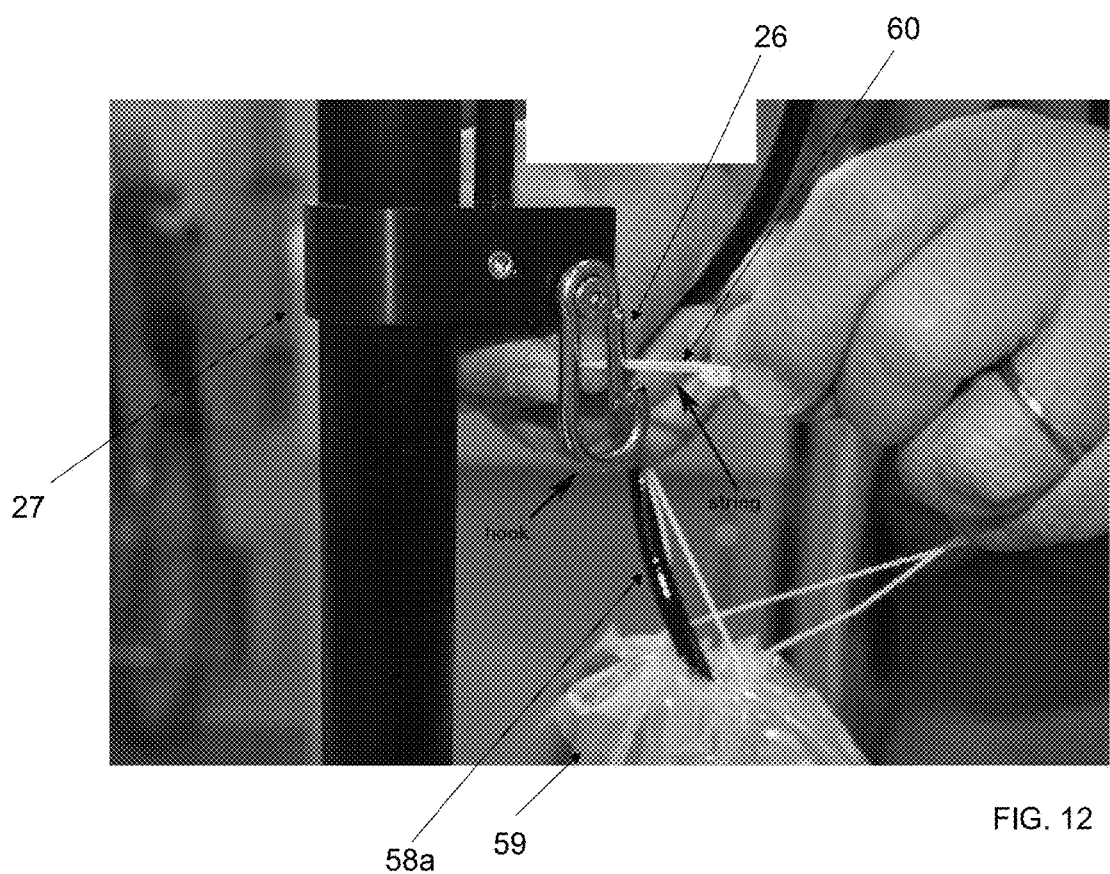
FIG. 12 shows the user of FIG. 11 connecting the drawstring to the hook of FIG. 10.

FIG. 10 shows the device of FIG. 1 where additional structure 58 extends from a junction housing 13 to section 58a and is gathered into a carrier bag 59 in section 58b, and the carrier bag 59 is suspended from a hook 26 extending by way of clamp 23 from a side of the protection tube 21, where drawstring 60 connects hook 26 with carrier bag 59. FIG. 11 shows a user having gathered the additional structure section 58b of FIG. 10 into the carrier bag 59 drawing closed a drawstring 60 at a top 61 of the carrier bag 59. FIG. 12 shows the user of FIG. 11 connecting the drawstring 60 to the hook 26 of FIG. 10.

Figure 13:
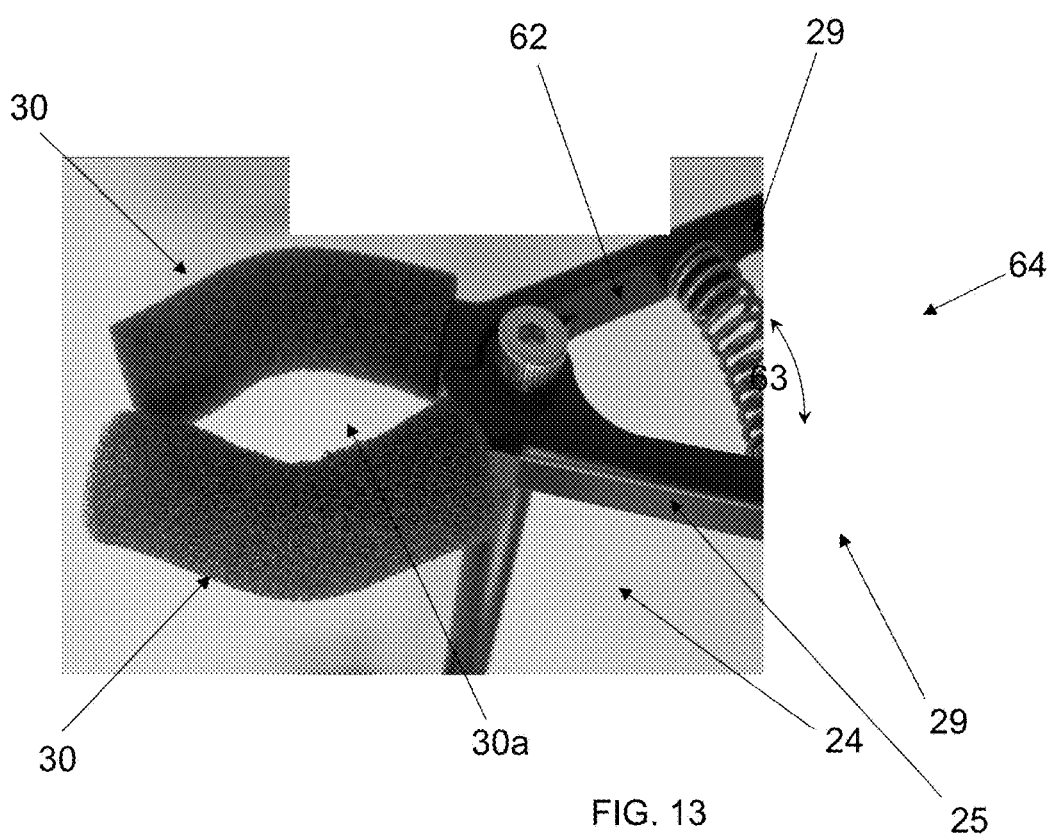
FIG. 13 is a top perspective view of a scope clamp of the upper support clamp of the device of FIG. 1.

FIG. 13 is a top perspective view of a scope clamp 25 of the upper support clamp of the device of FIG. 1, where padded jaws 30 comprise removable and disposable sponge cylinders to pad support of an upper structure of the bronchoscope in space 30a and protect from biological contamination (they are removed and disposed of at a cleaning and decontamination step after the procedure). Pivot point 62 is preferably also a top of support bar 24 for pivoting of handles 29 and padded jaws 30, where handles 29 are urged apart by spring 64 along path 63.

FIG. 15 is a cutaway side view of a magnetic support 28 of the invention device of FIG. 1, where bore 71 receives the protection tube and section 70 joins two halves, of which half 72 is one and bore 72a allows for a screw or bolt to pass through the two halves and tighten them about the protection tube. Magnet 31 comprises a holder 73 fixed to half 72 and to which magnet element 74 is connected.

FIGS. 16 and 17 are respectively a top and side view of a combined pole clamp and magnetic support 27 of the device of FIG. 1, as previously described in FIG. 3, where further bore 76 is adapted to receive the protective tube and break 77 is adapted to be closed by a screw or bolt to secure the clamp 27 to the protective tube. Opposing jaw 34 comprises an end 34a and defines a generally concave inside surface along with jaw 35 wherebetween an IV pole can be secured by causing threaded shaft 38 to rotate within a threaded bore in extension 36 by turning handle 37.

Figure 18:
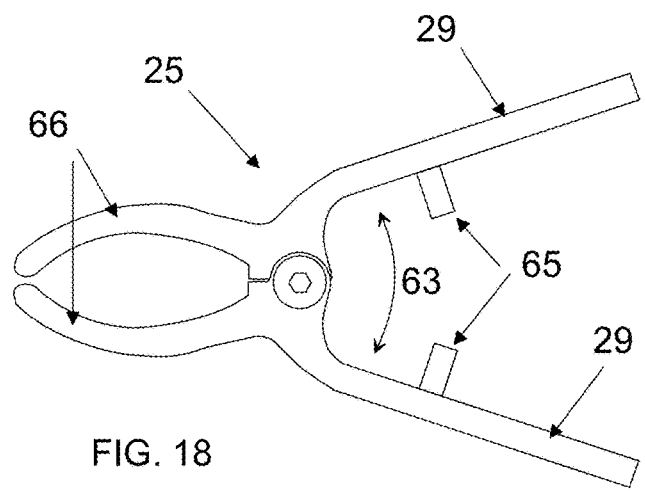
FIG. 18 is a top view of a scope clamp as part of an upper structure support clamp with disposable jaw covers and spring removed.
Figure 19:
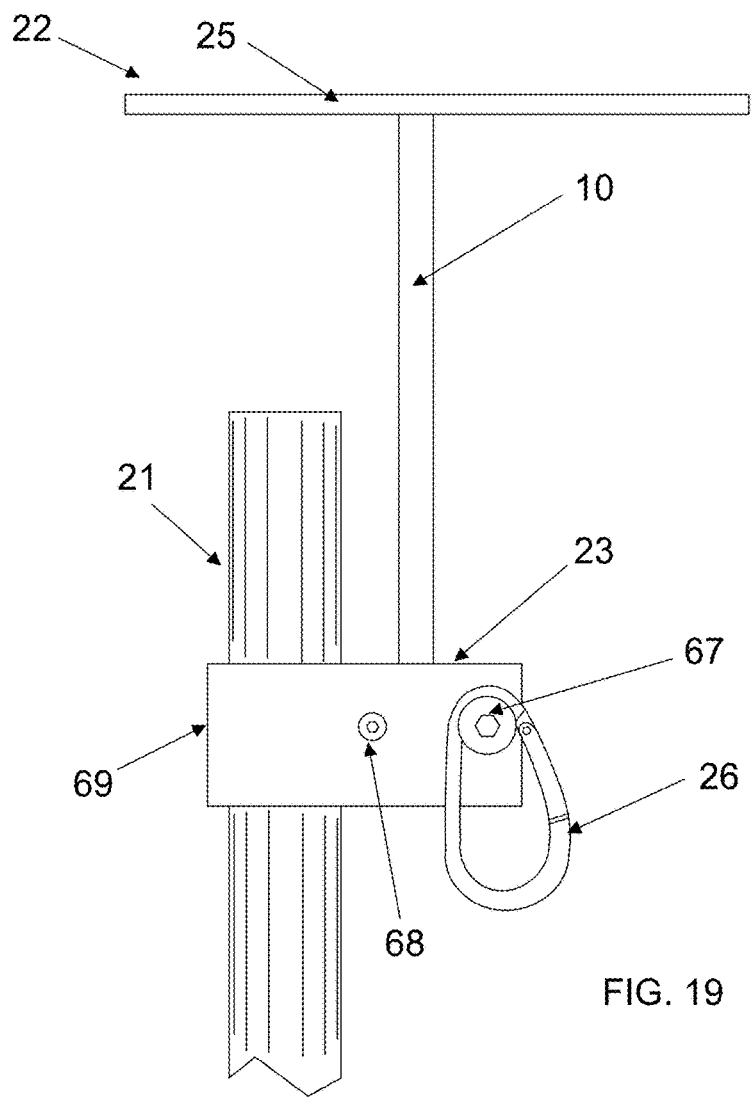
FIG. 19 is a side view of the upper structure support clamp and a portion of the protection tube.

FIG. 18 is a top view of a scope clamp 25 as part of an upper structure support clamp with disposable jaw covers removed showing bare jaws 66. FIG. 19 is a side view of the upper structure support clamp 21 and a portion of the protection tube 21, where support bar 24 is adapted to provide all support necessary to maintain an upper structure of the bronchoscope so that the insertion tube lies generally along an inside axis of the protection tube.

The following is a further general description of the invention storage and protection device. The invention storage and protection device is designed to enclose and protect the delicate device from damage during pre- and post-usage, transport, and storage. The device serves three major roles: 1) bronchoscope ergonomic mount and protector designed for use in the procedure suite or operating room, 2) transport enclosure designed to protect the delicate device during movement between locations, 3) long term storage device. If the insertion tube of the bronchoscope is not contained in the protection tube of the invention device, the insertion tube should, except for brief periods of transit, be used in a patient procedure or being cleaned and decontaminated, steps which are well known in the art. The invention device may be said to be made up of three major components: 1) a rigid tube structure, 2) a scope head clamp, and 3) anchoring elements.

Figure 6A:
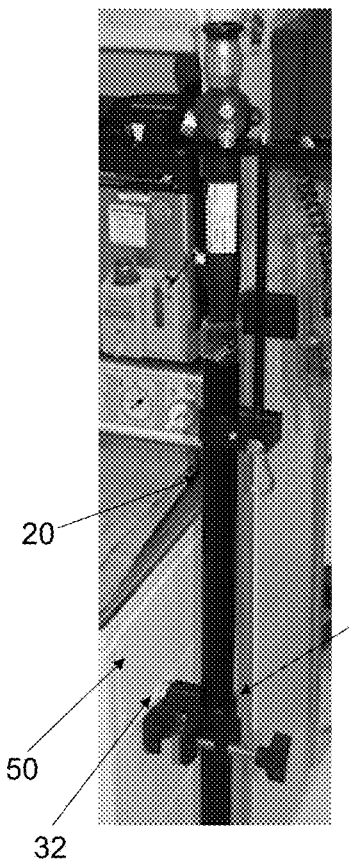
FIGS. 6A, 6B and 6C shows the device of FIG. 1 releasably and vertically engaged with different vertical metal surfaces, providing local and immediate access to the protected bronchoscope.
Figure 6B:
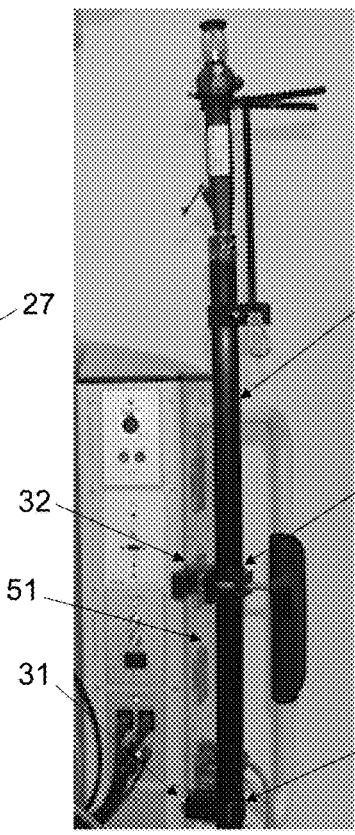
Figure 6C:
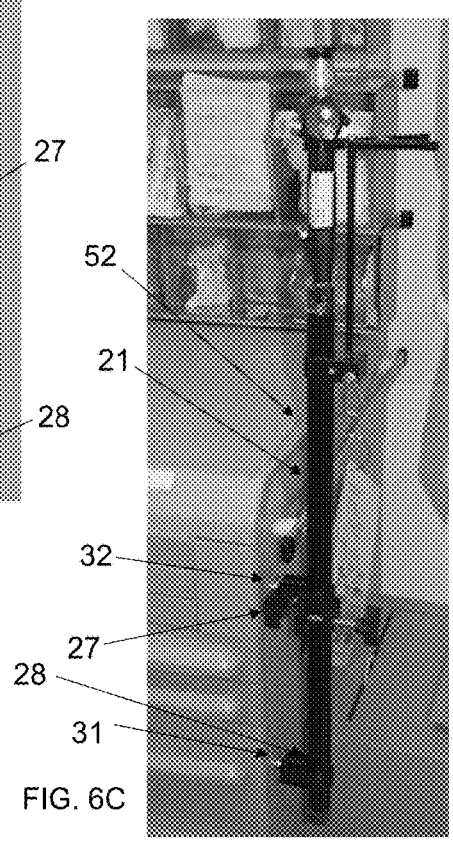

Providing only a vertical metal wall plate turns any location into a potential storage (long term or temporary) area for a bronchoscope engaged with the invention device, as seen in FIGS. 6A, 6B and 6C, respectively an anesthesia machine, a video boom, and an O.R. cart. When a bronchoscopy procedure is complete, the bronchoscope engaged with the invention device (preferably having a disposable, sealed liner protecting the internal surface of the protection tube), the bronchoscope and the invention device are transported to the decontamination room. The bronchoscope is then removed, decontaminated, and then re-placed in a decontaminated invention device, ready to restart the cycle of storage-transport-use-decontamination. An invention device which becomes biologically contaminated is sent to be decontaminated (via wash or autoclave), and then re-enters the pool, ready to transport and protect the next fiberscope. There will be different versions of the invention device offered to house different types of endoscopes. The standard form of the invention device will also be manufactured in different lengths and configurations in order to house a wide array of medical endoscopes. For instance, a longer version will house transesophageal-echo (TEE) probes. This invention device will attach to an ultrasound machine via a special clamp. Another model of invention device will contain a shorter tube because it will house a shorter scope used by otolaryngologists.

The invention device may have one or more of three disposable elements: 1) a plastic liner, 2) a carrier bag, or 3) foam clamp pads. The purpose of these elements is to prevent patient to patient cross-contamination, speed up the rate of device turnover and decontamination, and protect the bronchoscope components from damage. The plastic liner is a sleeve like bag that is inserted into the rigid tube with the help of an insertion wand. A flexible plastic liner is sealed at the bottom end, such that any secretions or bodily fluids cannot drip out during transport and use. The liner is designed to keep the inside of the rigid tube clean during use as it shields this surface from contamination by the endoscope. Once the procedure is over and the endoscope is removed for cleaning, the plastic liner is removed and disposed of.

The carrier bag is designed to carry a video-chip interface cartridge. Bronchoscopes with distal chip cameras as well as other endoscopes such as TEE probes have an electronic array built into the endoscope. Thus, they have a bulky connector that is used to plug them into their respective machine (camera and light source for a bronchoscope, vs. an ultrasound workstation for a TEE probe). This connector cartridge needs to be contained and protected during transport, as it can be easily damaged if it falls. The carrier bag is used to house the cartridge when the endoscope is being stored and transported. The cartridge is placed inside the bag and the strings are pulled tight to close the bag top. The strings are then hung onto the specialized spring-lock hook, which secures the cartridge carrier for transport. Once the endoscope is removed for cleaning, the bag is discarded. The foam clamp pads slide onto the jaws of the scope head clamp. This component serves two functions: 1) protect the fragile endoscope head/handle during use, and 2) reduce the probability of patient to patient cross contamination. The foam pads are tubular foam elements that are pulled over the clamp jaws; once applied, they are held in place by friction. After use, they are removed and discarded.

In an alternate form of the invention device, the protection tube is preferably formed of durable metal, such as aluminum or steel. However, it within the objects of the invention to form the protection tube of an appropriate polymer or plastic, including acrylic to permit visualization of the insertion tube while the bronchoscope is engaged in the invention device. Further, the protection tube may at least in part be formed of a disposable polymer tube, which disposability permits a user to virtually eliminate the chance of contamination between patient uses. Still further, the protection tube may be formed at least in part of a flexible polymer tube having fiber or other reinforcement therein.

A description of certain embodiments applicable to the concept of a thin, flexible liner comprising a generally cylindrical shape and adapted to lie between an inside surface and a protected insertion tube within the protection tube are as follows:

1. a first flexible liner shall be open from a top opening to a bottom opening, preferably so that part of the top and bottom ends can be folded over to an outside surface of the protection tube as the flexible liner extends beyond top and bottom ends (an elastic band optionally holds these folded over ends in place);

2. a second flexible liner shall be open from a top opening to sealed end which will be located toward the bottom opening of the protection tube, whereby the generally cylindrical liner will continue downward from the sealed end to a bottom en, preferably so that part of the top and bottom ends can be folded over to an outside surface of the protection tube as the flexible liner extends beyond top and bottom ends (an elastic band optionally holds these folded over ends in place);

3. a user is provided with collections or rolls each of the first flexible liner and the second flexible liner for use at appropriate times; and 4. a user is provided with a collection or roll of the first flexible liner, whereby a non-residue tape or alligator clamp (or other clamping means) are provided so that a user may un-fold a bottom end of the first flexible liner from the bottom end of the protection tube and either (a) gather and twist the bottom end of the flexible liner and thereafter tape the gathered or twisted part upward on an outside surface of the protection tube (thereby forming a sealed end) or (b) gather and twist the bottom end of the flexible liner and thereafter clamp the gathered or twisted part (thereby forming a sealed end).

The above design options will sometimes present the skilled designer with considerable and wide ranges from which to choose appropriate apparatus and method modifications for the above examples. However, the objects of the present invention will still be obtained by that skilled designer applying such design options in an appropriate manner.

We claim:

1. An assembly for storage and protection of a flexible bronchoscope with a flexible insertion tube comprising:
   (a) a protection tube with a top end, a bottom end and a bore defined within the protection tube substantially greater in diameter than that of an insertion tube of the flexible bronchoscope;
   (b) an upper structure support clamp fixed to the protection tube by a first clamp connector and extending above the top end of the protection tube by a support bar to support a scope clamp; and
   (c) the scope clamp being adapted to securely and releasably engage an upper structure of the flexible bronchoscope so that at least a majority of the insertion tube is located within the bore of the protection tube.

2. The assembly of claim 1 wherein the first clamp connector is fixed at an upper section of the protection tube.

3. The assembly of claim 2 wherein the first clamp connector is releasably fixed to the protection tube.

4. The assembly of claim 3 wherein an IV pole clamp is releasably fixed to the protection tube.

5. The assembly of claim 2 wherein two or more magnetic supports, each of the magnetic supports comprising a strong magnet element is fixed to the protection tube and is adapted to releasably engage a vertical metal surface from which to support an entire weight of the assembly and an engaged bronchoscope.

6. The assembly of claim 5 wherein the magnetic supports are releasably fixed to the protection tube.

7. The assembly of claim 6 wherein one of the magnetic supports are integral with an IV pole clamp adapted to releasably engage a vertical IV pole to support the entire weight of the assembly and an engaged bronchoscope.

8. The assembly of claim 1 wherein the first clamp connector is releasably fixed to the protection tube and is movable to multiple positions up or down on the protection tube to respectively raise or lower the scope clamp relative to the top end of the protection tube.

9. The assembly of claim 1 wherein the scope clamp comprises opposing jaws to engage the upper structure of the bronchoscope and the opposing jaws are padded with padding.

10. The assembly of claim 9 wherein the padding of the opposing jaws are disposable covers.

11. The assembly of claim 1 wherein a cylindrical flexible liner is located within the bore of the protection tube and is adapted to receive the insertion tube through a top opening.

12. The assembly of claim 11 wherein an upper part of the flexible liner extends through an upper opening of the protection tube and is folded back over the top end thereof.

13. The assembly of claim 12 wherein the flexible liner is sealed at a bottom section.

14. The assembly of claim 1 wherein an additional structure extends from the upper structure of the bronchoscope, is gathered in part into a carrier bag, where the carrier bag is suspended from a hook connector fixed to the protection tube.

15. The assembly of claim 14 wherein the carrier bag is disposable.

16. The assembly of claim 1 wherein the protection tube is formed of durable metal.

17. The assembly of claim 1 wherein the protection tube is formed of rigid polymer.

18. The assembly of claim 17 wherein the protection tube is disposable.

* * * * *